US005665238A

United States Patent [19]

Whitson et al.

[11] Patent Number: 5,665,238
[45] Date of Patent: Sep. 9, 1997

[54] METHOD AND APPARATUS FOR THE COLLECTION STORAGE AND REAL TIME ANALYSIS OF BLOOD AND OTHER BODILY FLUIDS

[75] Inventors: Peggy A. Whitson, El Lago; Vaughan L. Clift, Houston, both of Tex.

[73] Assignee: The United States of America as represented by the Administrator of the National Aeronautics and Space Administration, Washington, D.C.

[21] Appl. No.: 605,300

[22] Filed: Jan. 26, 1996

Related U.S. Application Data

[63] Continuation of Ser. No. 247,187, May 19, 1994, abandoned.

[51] Int. Cl.[6] .......................... B01D 37/00; B01D 61/00
[52] U.S. Cl. .......................... 210/649; 210/483; 210/488; 210/489; 210/490; 210/491; 210/496; 210/503; 210/504; 210/506; 210/508; 210/767; 422/73; 422/101; 422/104; 436/177; 436/178
[58] Field of Search .......................... 210/645, 767, 210/483, 488, 489, 490, 491, 946, 503, 504, 506, 508, 509, 649; 422/56, 57, 58, 59, 60, 61, 73, 101, 102, 104; 436/177, 178; 427/338, 414, 244

[56] References Cited

U.S. PATENT DOCUMENTS

| | | |
|---|---|---|
| 3,146,163 | 8/1964 | Brewer . |
| 4,678,757 | 7/1987 | Rapkin et al. .......................... 436/177 |
| 4,810,394 | 3/1989 | Masuda .......................... 210/767 |
| 4,816,224 | 3/1989 | Vogel et al. .......................... 210/767 |
| 4,933,092 | 6/1990 | Aunet et al. .......................... 210/729 |
| 5,135,719 | 8/1992 | Hillman et al. .......................... 210/503 |
| 5,139,685 | 8/1992 | de Castro et al. .......................... 210/767 |
| 5,207,984 | 5/1993 | Kheiri .......................... 422/58 |
| 5,240,862 | 8/1993 | Koenhen et al. .......................... 436/178 |
| 5,262,067 | 11/1993 | Wilk et al. .......................... 210/767 |
| 5,340,539 | 8/1994 | Allen et al. .......................... 422/56 |
| 5,364,533 | 11/1994 | Ogura et al. .......................... 210/767 |
| 5,423,989 | 6/1995 | Allen et al. .......................... 210/650 |
| 5,426,030 | 6/1995 | Rittersdore et al. .......................... 422/56 |
| 5,460,777 | 10/1995 | Kitajima et al. .......................... 422/56 |
| 5,460,974 | 10/1995 | Kozak et al. .......................... 436/177 |

*Primary Examiner*—John Kim
*Attorney, Agent, or Firm*—Hardie R. Barr

[57] ABSTRACT

The present invention provides an apparatus for separating a relatively large volume of blood into cellular and acellular fractions without the need for centrifugation. The apparatus comprises a housing divided by a fibrous filter into a blood sample collection chamber having a volume of at least about 1 milliliter and a serum sample collection chamber. The fibrous filter has a pore size of less than about 3 microns, and is coated with a mixture of mannitol and plasma fraction protein (or an animal or vegetable equivalent thereof). The coating causes the cellular fraction to be trapped by the small pores, leaving the cellular fraction intact on the fibrous filter while the acellular fraction passes through the filter for collection in unaltered form from the serum sample collection chamber.

3 Claims, 2 Drawing Sheets

FIGURE 2

Electrolytes

| | | Protocol |
|---|---|---|
| Sodium | R* | 1 & 2 |
| Chloride | R | 1 & 2 |
| Potassium | R | 1 & 2 |
| Calcium | R | 1 & 2 |
| Magnesium | R | 1 & 2 |
| Phosphate | L** | 1 & 2 |

Metabolites

| | | |
|---|---|---|
| Glucose | R | 1 & 2 |
| Urea | R | 1 & 2 |
| Cholesterol | R | 1 & 2 |
| Uric acid | L | 1 & 2 |
| Tri glyceride | R | 2 |
| Total protein | R | 1 & 2 |
| Total Bilirubin | R | 1 & 2 |
| Creatinine | R | 1 & 2 |
| Blood urea nitrogen | R | 1 & 2 |

Enzymes

| | | |
|---|---|---|
| Aspartate Transaminase | L | 1 & 2 |
| Alkaline Phosphatase | R | 1 & 2 |
| Alanine transaminase | L | 1 & 2 |
| Gamma glutaryl transferase | R | 1 & 2 |
| Amylase | L | 1 & 2 |
| Lactate dehydrogenase | L | 1 & 2 |
| Creatinine kinase | L | 1 & 2 |

Hormones and related enzymes

| | | |
|---|---|---|
| Thyroxine | R | 1 |
| Insulin | R | 2 |
| Cortisol | R | 1 & 2 |
| Atrial naturetic factor | R | 2 |
| Angiotensin | R | 1 & 2 |
| Melatonin | R | 2 |

---

*"R" Recovered fully.
**"L" recovered but at a lower level than frozen serum.

METHOD AND APPARATUS FOR THE COLLECTION STORAGE AND REAL TIME ANALYSIS OF BLOOD AND OTHER BODILY FLUIDS

This application is a continuation of application Ser. No. 08/247,187, filed May 19, 1994, now abandoned.

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 U.S.C. 2457).

FIELD OF THE INVENTION

The present invention provides a simple, inexpensive method and apparatus for passively separating cellular (or solid) and acellular fractions of clinically useful volumes of bodily fluids, for substantially simultaneously or subsequently analyzing said bodily fluids for one or more analytes, and for prolonged preservation of said analytes.

BACKGROUND OF THE INVENTION

One of the primary means used to diagnose the state of a person's health is to analyze the person's blood or other bodily fluids for the presence or absence of "analytes" indicative of the person's health. An "analyte" is any substance contained in a bodily fluid for which either knowledge of the presence or concentration is desired for clinical or laboratory purposes, or for which the substance itself is retained and used for some other analytical or pharmacological purpose. Analytes such as hormones, salts, enzymes, ketones, glucose, drugs, infectious agents, etc., indicate whether the person has contracted an infection and/or whether the person's glands and/or other organs are functioning effectively.

Certain bodily fluids, such as urine, saliva, semen, etc. can be obtained non-invasively, and analysis of such fluids can provide information about the state of a person's health. Some analytes will be found only in certain bodily fluids, such as cerebrospinal fluid. However, the bodily fluid that typically gives the most complete picture of a person's health is whole blood.

One difficulty encountered in analyzing many bodily fluids, such as whole blood, is that the "fluid" actually is composed of both solid and liquid components. For example, whole blood is composed of two fractions. One fraction is a "cellular" fraction, which includes the various types of blood cells and any other relatively "solid" matter found in the blood. The other fraction is an "acellular" fraction which consists of plasma or serum. Most of the "analytes" of interest are contained in the acellular fraction.

In order to obtain the most accurate analysis of the blood, it is important to separate the analytes from the cellular fraction of the blood relatively quickly after the sample is drawn. Otherwise, the quantity and or quality of various analytes in the blood may be altered by the cellular fraction, e.g., by metabolism, release of intracellular content, and/or simple dilution.

For similar reasons, the manner in which the cellular fraction is separated from the acellular fraction of the blood is important in order to avoid contamination of the acellular fraction with components from the cellular fraction. For example, the separation process, itself, can cause the cells in the sample to lyse and release the intercellular content into the sample, thereby contaminating the sample.

Methods for separating clinically useful volumes of blood generally require the blood to be collected, transferred into a glass or plastic vial, and then centrifuged at high speed for a period of time. Centrifugation causes the cellular or solid fraction of the sample to collect at the bottom of the vial and the acellular supernatant plasma or serum to collect at the top of the vial. The supernatant then can be decanted and analyzed. Sometimes, the vial is provided with a medium density inert gel which—due to its specific gravity—substantially isolates the cellular from the acellular fraction when centrifuged, permitting the components to be frozen and stored together.

Centrifugation and subsequent refrigeration of samples is sufficient to preserve the integrity of a sample of blood or other bodily fluid for a sufficient period of time in most cases. However, the process is cumbersome and expensive because it requires the blood or other sample either to be collected in a location having all of the proper equipment, or that the sample be refrigerated and transferred to a separate laboratory for further processing. Also, a substantial amount of time is required to obtain the results of the analysis. Time may be critical to the life or health of the patient; therefore, a more rapid, less expensive, less cumbersome method is needed to analyze samples of blood and/or other bodily fluids.

Some methods exist for separating and analyzing very small volumes of blood or other bodily fluids in situ. Typically, these methods involve exposing the blood or other sample to a porous membrane or a porous mat of glass, fiber, or a polymer of plastic, protein, or carbohydrate, which traps the cellular components (or solids) but permits the plasma to flow through onto a paper or plastic strip where the plasma is reacted immediately with analytical reagents.

Unfortunately, current methods and devices used for in situ analyses produce only a very small volume of serum or plasma which can be used only to measure one or a limited number of small analytes, such as glucose, electrolytes, and pH. The sample of blood must be small—typically less than 100 microliters. Because the entire sample is reacted immediately with the testing reagent(s), the entire sample is disposed of after it has been used for this limited purpose. None of the sample can be stored or used for any other testing.

The in situ separation devices in current use often either do not separate the sample into cellular and acellular fractions, or they separate the serum into subfractions, thereby altering the biochemistry of the serum. Also, the type of analyses that can be performed using such devices typically is a one stage procedure. The analyte is mixed with one or a number of reagents simultaneously to produce a color change or chemical reaction. Because these devices lack a supportive matrix and a path through which the sample can pass before further analysis, they cannot be used to perform a multiple stage analysis capable of measuring complex molecules, such as hormones, enzymes, antibodies, or viral particles. In addition, the accuracy of such analyses is impaired by the presence of hemoglobin, which is freed by the hemolysis or rupture of red blood cells in the sample.

The current methods used to test bodily fluids in situ also lack a convenient means for prolonged storage of viable samples. Currently, samples of bodily fluids must be refrigerated at or below $-20°$ C. in order to maintain the biochemical integrity of the sample. If the sample is to be tested for certain short lived or delicate analytes, preservatives and/or acids often must be added to preserve the integrity of the analytes.

Some tests permit whole blood samples to be stored on blotting paper dried in air—for example, for neonatal purposes. However, these dried samples: can be used only to test qualitatively for a limited number of analytes; cannot be used for quantitative testing; and, only remain viable for testing for about two weeks. The short term viability for such dried samples largely results because the blood cells tend to rupture and contaminate the sample with intracellular contents during the drying process. The free hemoglobin released in the rehydration process also interferes with many colorimetric assays.

Some analytes, such as insulin, can be preserved in a desiccated state by freeze drying the analyte under a vacuum. Unfortunately, a significant number of analytes that can be preserved in a desiccated state denature at some point during the process. Therefore, freeze drying of analytes is only of limited use to test for analytes that do not denature.

An accurate, efficient process for in situ collection, separation, testing, and storage of bodily fluids, such as blood, which can be used for a broad spectrum of analytes would be highly desirable.

SUMMARY OF THE INVENTION

The present invention provides a simple, portable, relatively inexpensive apparatus for accurately and efficiently collecting, separating, testing, and even storing between about 1–20 ml, preferably between about 1–10 ml, of blood or other bodily fluid in situ. The apparatus includes a collection chamber bounded on its sides by an opening in a sheet of material, preferably clear plastic, abutting a filter card. The filter card is made of fibrous material, preferably glass fiber material less than about a millimeter thick, having an average pore size of less than about 3 microns, more preferably less than about 1 micron. The fibrous material is treated with a carbohydrate/protein mixture which contains between about 1–40% wt/vol carbohydrate and about 0.1–15% wt/vol non-specific protein, preferably between about 10–20% carbohydrate and about 5–8% protein. A preferred carbohydrate/protein mixture comprises about 10% mannitol and about 6% albumin. The blood or other fluid moves through the filter card by capillary action aided by an absorbent matrix that has a high Klemm factor which abuts the filter card. The absorbent matrix and/or filter card can be treated with a wide spectrum of test reagents. The speed, cleanliness, and efficiency of the separation process can be altered by: (a) changing the absolute concentration of the carbohydrate/protein mixture; (b) applying positive or negative pressure to one side of the filter; and/or (c) varying the relative density and pore size of the filter card and absorbent matrix.

BRIEF DESCRIPTION OF THE DRAWINGS

FIG. 2 is a compilation of the results from Examples 1 and 2.

DETAILED DESCRIPTION OF THE INVENTION

Figure 1:
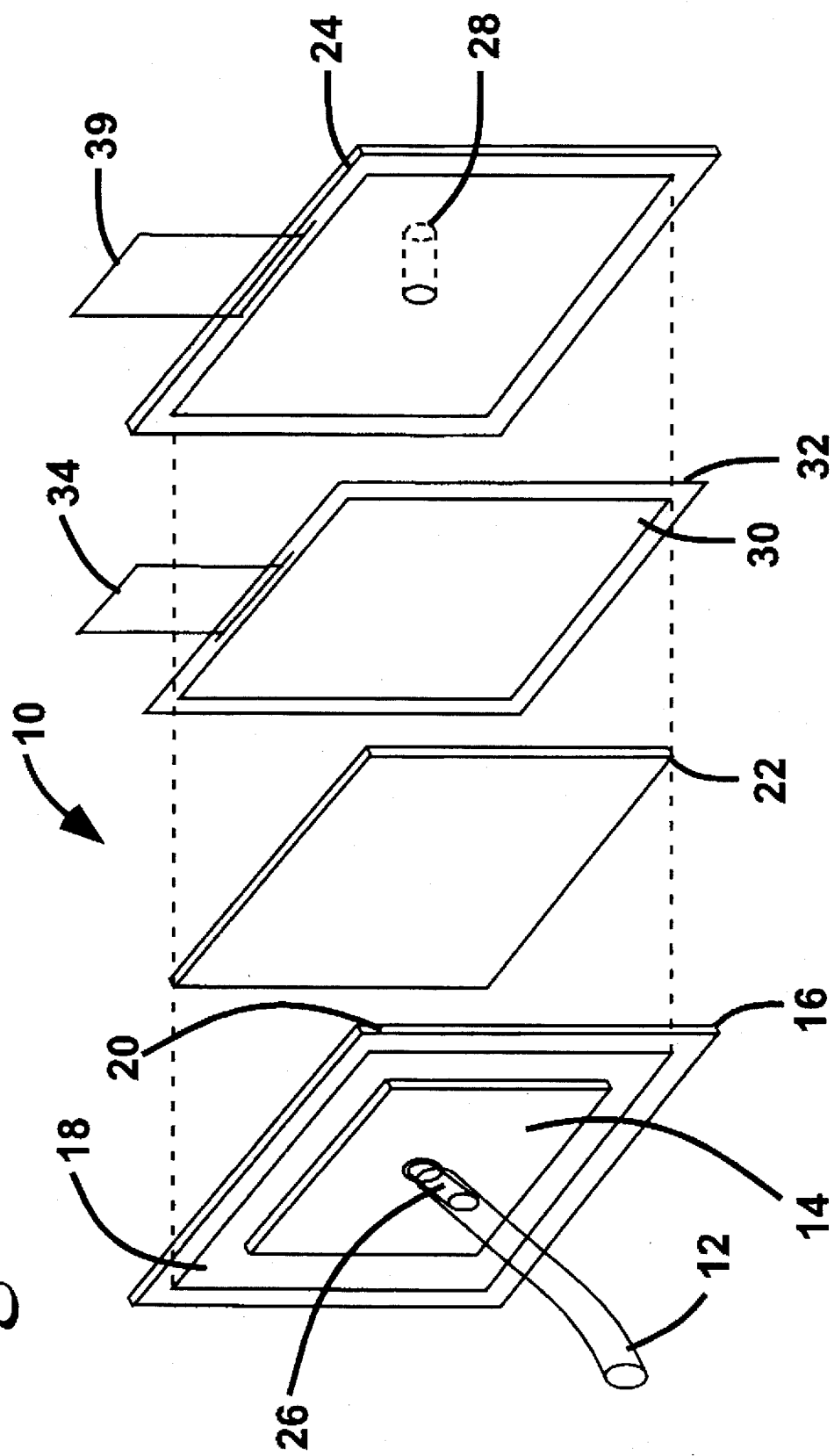
FIG. 1 is an exploded perspective view of the apparatus of the invention.

For ease in description, the method and apparatus of the present invention will be explained with reference to the separation and analysis of whole blood. However, the present invention is not limited to whole blood. The invention also may be used to separate and test other bodily fluids in situ, whether of human or animal origin. Such bodily fluids include, but are not limited to, blood, urine, saliva, tears, menstrual fluid, ascitic fluid, peritoneal fluid, joint fluid, cerebrospinal fluid, semen, transudate, or exudate. Knowing the particular body fluid and the type of analyte to be tested, a person of skill in the art can determine the appropriate parameters in light of the following description.

Referring to FIG. 1, the apparatus 10 of the present invention comprises tubing 12 or other means for transferring a bodily fluid of interest into a collection chamber 14 formed by an opening in a substantially flat or planar shell 16. The shell 16, which is preferably made of a relatively inert clear plastic, has flanges 20 at its outer edges which extend toward a filter card 22. The surface area of the shell 16 adjacent to the filter card 22 is slightly larger than the surface area of the filter card 22, so that, once the apparatus 10 is assembled, the flanges 20 house the filter card 22 substantially abutting the opening in the shell 16. The sides of the blood sample collection chamber 14 comprise the sides of the opening in the shell 16 and the bottom of the chamber 14 comprises the abutting filter card 22. The filter card 22 should be positioned so that the blood or other bodily fluid that is deposited in the collection chamber 14 covers substantially the entire surface of the filter card 22 to infiltrate substantially the entire filter card 22.

The filter card 22 may be composed of any suitable fibrous material having a large surface area, an appropriate density, and an appropriate average pore size. In a preferred embodiment, the filter card 22 is made from glass fiber, which has a larger surface area than most fibers, permitting the use of a smaller volume of fibrous material to separate the components of the fluid. For whole blood, a desirable average pore size is less than about 3 u, preferably about 1 u, and a desirable density, if the filter card is made from glass fiber, is a basis weight of about 465 gm/m$^2$. Of course, the density will change with the weight of the fibrous material; however, lighter materials generally are preferred due to their portability. A preferred embodiment uses #32 Glass Fiber Filter, Catalog #08090, obtained from Schleicher and Schuell (Keene, N.H.). Other suitable materials for the filter card 22 include, but are not limited to, cellulose fibers, natural organic fibers, semi synthetic fibers, synthetic fibers, and hydrophilic polymeric gels.

The filter card 22 should be treated with a protein/carbohydrate mixture comprised of between about 1–40% wt/vol carbohydrate mixed with 0.1–15% wt/vol non-specific protein, preferably about 10%–20% wt/vol carbohydrate and about 5–8-% wt/vol protein. A preferred embodiment uses about 10% wt/vol mannitol and about 6% wt/vol albumin.

Preferred carbohydrates include: monosaccharides, such as fructose, galactose, and glucose; disaccharides, such as mannitol, lactose, and sucrose; and, complex polymeric sugars, such as starch and glycogen. Preferred proteins include human plasma fractions, such as albumin, globulin, transport proteins, and low molecular weight animal and vegetable equivalents. The filter card 22 preferably is treated with the protein/carbohydrate mixture by dipping the filter card 22 in a solution of the protein/carbohydrate solution and then air drying the filter card 22.

Treatment of the filter card 22 with the protein/carbohydrate mixture significantly improves the efficiency of separation and permits the separation of relatively large volumes of whole blood up to about 20 milliliters. The amount of blood that can be separated is limited only by the size of the apparatus 10. The relative proportion, absolute amount, and composition of the carbohydrate/protein mixture provides variable and optimal control of the separation process while preventing cell lysis. The speed, cleanliness, and efficiency of the separation process can be altered by: (a) changing the absolute concentration of carbohydrate and/or protein in the mixture; (b) applying positive or negative pressure to one side of the filter card 22; and/or (c) varying the relative size of pores in the filter card 22 and absorbent matrix 30.

The "efficiency" of the process generally refers to the ability of the process to extract the largest percentage of available serum or acellular fluid contained in a particular sample. The apparatus and method of the present invention normally recovers approximately 80–100% of the serum in whole blood. The "cleanliness" of the process refers to how effectively the process screens the serum or fluid of cells and/or other solids. Generally, increasing the concentration of carbohydrate in the solution used to coat the filter card 22 increases the efficiency and cleanliness of the separation but decreases the speed of the separation. Therefore, a higher concentration of carbohydrate, in the range of 10–20% wt/vol, normally is preferred as long as the analytes to be tested will survive for about 30 minutes to about 1 hour. Some analytes are extremely delicate and/or have extremely short half lives. In order to test for such analytes, it may be necessary lower the concentration of carbohydrate somewhat and accept a lower level of efficiency and cleanliness of the process. In some cases, a preserving agent may be added to to the sample before beginning the separation process in order to preserve such analytes. Another way to preserve some short lived analytes might be to include an antibody for the analyte on the absorbent matrix 30. The binding of the analyte to the specific antibody, itself, may preserve the analyte for further analysis.

After passing through the filter card 22, the plasma fraction reaches a serum sample collected chamber which may contain an absorbent matrix 30 preferably positioned in direct contact with the filter card 22. The absorbent matrix 30 should be made from a material having a relatively high "Klemm" factor, on the order of at least about 15, preferably about 30–70. The higher the Klemm factor, the more passive force will be exerted on the sample to draw the sample through the filter card 22. The Klemm factor should be as high as possible without causing blood cells or other solid matter to flow through the filter card 22. In a preferred embodiment, the absorbent matrix 30 is Plasma Card Grade 900, a cellulose filter having a Klemm factor of about 64, obtained from Schleicher & Schuell (Product #56630). Other suitable materials for the absorbent matrix 30 include, but are not limited to, sepharose gel, agar, and glass fiber matting.

Once assembled, the flanges 20 adhere to a back plate 24, preferably forming a substantially water tight seal around the filter card 22 and absorbent matrix 30 using any suitable means known in the art. Although a substantially water tight seal is preferred, the invention does not require a tightly sealed filter in a pressure vessel, as do many other techniques.

The tubing 12, or other means used to deposit the bodily fluid in the collection chamber 14, may be directly connected to a venous catheter or other access or collection port for blood or another bodily fluid. In this way, the fluid sample can be immediately deposited in the collection chamber 14 and analyzed substantially as it is collected. If the fluid is blood, direct transfer of the fluid to the collection chamber 14 obviates the need for anticoagulation. If tubing is used, the tubing 12 preferably is engaged with a plate 18 which has a suitable adapter 26, such as a male Luer port.

The transfer of such fluid into the collection chamber 14 can be aided, if desired, by aspiration with a syringe using an aspiration port 28 in the back plate 24. The aspiration port 28 may have any suitable construction which is compatible with an aspiration syringe. For example, the port may be a female Luer port which extends away from the body of the apparatus 10. The aspiration port 28 preferably should be sealed using any known means capable of maintaining the water tight seal within the apparatus 10, but also permitting disruption of the seal if aspiration is desired.

The separation process may be continued until the filter card 22 and/or the absorbent matrix 30 is filled. The blood or other bodily fluid is drawn by the high Klemm factor of the absorbent matrix 30 and passes through the filter card 22 by capillary action independent of gravity. The passive operation of the apparatus 10 is advantageous because one of the contemplated uses for the invention is to collect, separate, and store blood or other bodily fluids during space flight in the absence of gravity. In addition, capillary action does not require a centrifuge or other cumbersome equipment to separate the bodily fluid. Compared to the glass or plastic vials and powered equipment required to separate bodily fluids by centrifuge, the apparatus 10 of the present invention is extremely portable.

The absorbent matrix 30 preferably is supported in a frame 32 made of any suitable material, preferably a relatively inert clear plastic. The absorbent matrix 30 and the back plate 24 preferably are provided with pull-tabs 34. When the filtration process is complete, the pull-tabs 34 permit the removal of the absorbent matrix 30 from the apparatus 10 without the need for direct contact which could contaminate the absorbent matrix 30.

The absorbent matrix 30 and/or the filter card 22 may be impregnated with any number of suitable reagents to test for particular analytes, including well known reagents used to conduct specific antibody mediated assays, enzyme mediated assays, ligand mediated assays, and binding resins. As already alluded to, the filter card 22 and/or the absorbent matrix 30 also may be impregnated with specific chemicals and/or antibod(ies) which will preserve delicate or short lived analytes for later extraction and analysis. Also, because the separation process can begin substantially simultaneously with the collection of the bodily fluid, biochemical changes in the concentration and/or structure of analytes due to the presence of a cellular fraction are minimized or eliminated. For example, the cellular fraction is not available to consume glucose or other consumable analytes in the sample. The preservation of short lived and/or delicate analytes can be enhanced by prechilling the apparatus 10 before use, and/or by transferring the apparatus 10 to a cooled environment as soon as possible during or after the separation process.

The absorbent matrix 30 may be used and/or stored in a number of different ways. In a preferred embodiment, the absorbent matrix 30 is dried by subjecting the matrix to a flow of dry air which preferably should not exceed body temperature. Above about 40° C., enzymes and other delicate analytes on the absorbent matrix 30 tend to degrade. Once dried, the absorbent matrix can be placed in a container with a desiccant and an oxygen scavenger, such as an activated cuprous compound, to reduce the water content and oxygen tension in the surrounding atmosphere. Preferably, the oxygen content of the air surrounding the sample should be maintained as close as possible to 0%. The sample also preferably should be isolated from light. Otherwise, the sample may be stored in ambient conditions. The addition of standard anti-peptidase chemicals, antioxidants, and/or preservatives will protect certain analytes whose concentrations may be altered in the drying process. Compared to other available methods for storing such samples, the procedures required to preserve and store the absorbing matrix 30 in robust condition are simple, inexpensive, and portable.

Storing bodily fluids on the absorbent matrix 30 can preserve a broad range of the analytes for clinical and research purposes for extended periods of at least days to weeks. In fact, some analytes which are very difficult to preserve by freezing have been preserved using the present invention.

The use of a clear plastic shell 16, flanges 20, and back plate 24 will result in an additional advantage. The clear plastic will permit the filtration process to be observed. An end point for the process can be selected by choosing an acceptable time, determined partly by the design of the filter and the fluid being absorbed or by watching the area of discoloration of the absorbing matrix 30 through the back plate 24. Furthermore, the chemical testing reagent(s) can be impregnated onto either the absorbent matrix 30 or both the absorbent matrix 30 and/or the filter card 22 and then a color change, agglutination, or other process taking place on the absorbing matrix 30 can be observed through the clear plastic. In addition, the assay may be by direct fluoroscopy, spectroscopy, or thermal or electrical impedance. The latter will require the incorporation of appropriate electrodes into the plastic back plate.

The apparatus 10 also can be adapted so that the results can be quantified. For example, a line of reagent "dots" may be engineered into the apparatus 10 so that the dots react to a specific concentration of analyte. After reaction, the dots may be compared to a scale which will quantify the results of such reaction. For example, the dots could be engineered to change color either absolutely or to an intensity that relates to the concentration of a particular analyte in the sample. The color of the dots after the reaction could be used to extrapolate the concentration of the analyte present in the whole blood, e.g., by comparison to a color scale which may be separate from or incorporated into the apparatus.

If a series of dots is used, the reagent dots may be a specific chemical, such as a dye which changes color with pH or with the progress of an enzymatic process or cascade. For example, such a dot could be capable of detecting glucose through the action of the enzyme glucose oxidase. In a preferred embodiment, the "dot" detects an antibody mediated reaction which is specific to an analyte or a group of analytes. The antibody specifically binds to the analyte in the absorbing matrix and initiates a cascade of immunochemical reactions which produce an observable change.

In another preferred embodiment of the device, the antibody may be loosely bound in the filter card 22, itself, and therefore may pass through only with the passage of an analyte. Or, the antibody may be free in the filter card 22 or the collection chamber 14 such that the antibody is bound to a cell and does not pass through into the absorbent matrix 30 to initiate an identifying cascade. Any number of variations may be made to adapt test reagents for use in the present invention.

The invention will be more clearly understood with reference to the following examples.

EXAMPLE 1

In this experiment (Protocol 1), blood was collected from a crewmember on the Space Shuttle into both a vacutainer and into the dried-blood collection device of the present invention. After insertion of an appropriate venous cannula or butterfly using standard procedures, the vacutainer adapter was attached and two 5 ml samples of whole blood were collected into two 5 ml vacutainer tubes. The venous line was occluded and the vacutainer adapter removed.

A blood collection device was attached to the cannula and inspected visually while it was filling. The operator was able to look through the clear casing of the blood collection device and observe the filling of the chamber with blood. After the chamber filled completely, the venous line again was occluded. The process was repeated until five blood-collection devices were filled. The cannula then was sealed or removed.

The collection devices were fitted with velcro tabs to anchor them to the working area and set aside for about one hour. After completion of the blood collection, the blood collection devices were inspected, and any droplets floating free in the chamber behind the absorbent material noted. If free fluid was present, the blood-collection device was moved to the drop until the drop was absorbed onto the absorbent material. When no free droplets were visible, the blood collection device was opened and the absorbent material containing the plasma was removed by pulling the tab. The casing of the blood-collection device was closed and the entire unit was discarded. The card then was transferred into the drying box where it slid down into grooves that supported and spaced the cards. The process was repeated for all 5 cards. A fan in the drying box was turned on and the cards were dried in a flow of room air for about 2 hours. At the end of the 2 hours, the fan was turned off and the dessicant and oxygen scavenger was activated by removing the protective cover for these materials. The lid of the drying box was then closed and the cards were left in the box for storage.

The two vacutainer samples were placed in a centrifuge and cells and plasma were separated according to established procedure. The vacutainers then were placed in approximately −20° C. refrigeration and the time and date recorded. The entire unit was stowed for the remainder of the mission.

After landing, the frozen serum was removed within 8 hours and transferred to a refrigerated transfer canister. The dried cards in stowage also were retrieved and all samples returned for postflight analysis. Two days after landing, the serum was thawed, the dried cards were rehydrated, and the serum was extracted. The rehydration process involved removing the card from its plastic support frame, folding the card, placing the card inside a 10 ml tube, adding a set quantity of distilled water, rotating the tubes for 5 minutes and then extracting serum from the moistened paper by compressing the paper with the plunger of the syringe and emptying the sample into the glass tube.

The two sets of serum were analyzed simultaneously for the molecules shown in FIG. 2. The majority of analytes were measured in an automated CX 5 biochemistry unit obtained from Beckman Instruments (Brea, Calif.) using a combination of amperometric and photometric methods. Most of the hormones are analyzed by radioimmunoassay using commercially available methods.

During the in-flight phase of the study, a ground-based control was run in which blood was drawn from two individuals using the same protocol and stored frozen or dried onto the card in the same way. The ground-based samples were subjected to conditions that were as similar to those of the in-flight samples as practical and were thawed or extracted and analyzed at the same time.

Data from the in-flight samples and ground-based controls were analyzed for mean, standard deviation, and coefficient of variation. Results from in-flight samples stored frozen were compared to results from the dried stored samples. The results are shown in FIG. 2.

The dried-blood-chemistry method provided accurate correlation to frozen samples taken in flight. In addition, the dried blood chemistry results show, in ground-based studies, a high correlation with samples of the same serum tested fresh.

EXAMPLE 2

Serum for this experiment (Protocol 2) was collected and pooled. Known quantities of certain analytes were added to artificially increase the concentrations to allow for some degradation before the experiment was begun and to give a broad representative group of all of the subcomponents of serum. The pooled serum with "spiked" concentrations of certain molecules, including melatonin, angiotensin, antidiuretic hormone, and atrial naturetic factor, was filter sterilized, and loaded into 17 syringes two days before launch. Thirteen of the syringes contained the exact volume known to be held by the cards from ground-based studies, one contained about 3 mls of the correct volume, and five contained about 7 mls of the known volume. The remaining two 5 ml syringes served as controls, and were stored frozen after the fluid had been placed on the cards.

Each syringe was capped and wrapped in Teflon tape to prevent leakage if broken. Each syringe was labeled with a code number and had a matching storage card similarly labeled. The syringes and cards were stored inside a semi-rigid "NOMEX" (thick cloth) bag inside of a −20° C. freezer. A drying box identical to the box used in the first experiment also was flown.

On a flight day early to midway through the mission, the syringes and cards were removed from their protective bags and each syringe was emptied in sequence onto its paired storage card. The emptied syringes were discarded. The two remaining syringes were stored frozen and the time and date were recorded. The cards were transferred to the "drying box" and the drying box fan turned on for about 2 hours. At the end of this period, the "rip-top" desiccant and oxygen scavenger container were opened and the drying box closed. The entire drying box, with cards inside, were placed inside a second plastic bag. The bag was sealed, and the entire unit was stowed in a middeck locker for the duration of the mission. After landing, the samples were handled as described in Example 1.

The dried-blood-chemistry method provided accurate correlation to frozen samples taken in-flight. In addition, the dried blood chemistry results showed, in ground-based studies, a high correlation with samples of the same serum tested fresh.

The invention has been described in connection with a particular embodiment. One of skill in the art will appreciate that many modifications may be made to the embodiment described herein without departing from the spirit of the present invention. Accordingly, the embodiment described herein is illustrative only and is not intended to limit the scope of the present invention.

We claim:

1. Apparatus for passively collecting and separating into cellular and acellular fractions, a blood sample having a volume of up to about 20 milliliters, comprising:
   a housing having at least one opening therethrough for receiving said blood sample;
   a fibrous filter dividing said housing into:
      a blood sample collection chamber having a volume of at least about 1 ml, said blood sample collection chamber being in fluid communication with said opening; and
      a serum sample collection chamber;
   said fibrous filter comprising a first surface, substantially all of which fluidly communicates with a blood sample in said blood sample collection chamber, a second surface abutting and fluidly communicating with said serum sample collection chamber, and an intermediate portion having a given height sandwiched between and in fluid communication with both said first and said second surfaces;
   wherein said acellular fraction of said blood sample is filtered from said blood sample collection chamber, across said first surface, across said intermediate portion, and across said second surface into said serum sample collection chamber; and
   wherein said fibrous filter has a pore size below about 3 microns and is coated with a mixture comprising between about 1–40% mannitol and between about 0.1–15% albumin; and
   an absorbent matrix in fluid communication with said serum sample collection chamber.

2. A method for passively separating into cellular and acellular fractions a blood sample having a volume of up to about 20 milliliters, comprising the steps of:
   providing a housing comprising at least one opening therethrough for receiving a blood sample;
   providing a fibrous filter comprising a first surface, substantially all of which fluidly communicates with a blood sample in said blood sample collection chamber, a second surface abutting and fluidly communicating with said serum sample collection chamber, and an intermediate portion having a given height sandwiched between and in fluid communication with both said first and said second surfaces, wherein said fibrous filter has a pore size of about 3 microns or less and is coated with a mixture comprising between about 1–40% mannitol and between about 0.1–15% albumin; and
   separating said blood sample into cellular and acellular fractions by filtering said blood sample from said blood sample collection chamber, across said first surface, across said intermediate portion, and across said second surface into said serum collection chamber and onto an absorbent matrix.

3. The method of claim 2 wherein said blood sample comprises a volume of between about 1–20 milliliters.

* * * * *